US008921063B2

(12) United States Patent
Pepe et al.

(10) Patent No.: US 8,921,063 B2
(45) Date of Patent: Dec. 30, 2014

(54) ENHANCING ENDOTOXIN DETECTION

(75) Inventors: Michael G. Pepe, Birmingham, AL (US); Milton Keith Champion, Hoover, AL (US)

(73) Assignee: BioDtech, Inc., Birmingham, AL (US)

( * ) Notice: Subject to any disclaimer, the term of this patent is extended or adjusted under 35 U.S.C. 154(b) by 0 days.

(21) Appl. No.: 14/001,740

(22) PCT Filed: Feb. 28, 2012

(86) PCT No.: PCT/US2012/026935
§ 371 (c)(1),
(2), (4) Date: Aug. 27, 2013

(87) PCT Pub. No.: WO2012/118800
PCT Pub. Date: Sep. 7, 2012

(65) Prior Publication Data
US 2013/0330759 A1  Dec. 12, 2013

Related U.S. Application Data

(60) Provisional application No. 61/447,581, filed on Feb. 28, 2011.

(51) Int. Cl.
*C12Q 1/37* (2006.01)
*C12Q 1/04* (2006.01)

(52) U.S. Cl.
CPC ............. *C12Q 1/04* (2013.01); *G01N 2400/50* (2013.01); *G01N 2800/709* (2013.01); *C12Q 1/37* (2013.01)
USPC ......................................................... 435/23

(58) Field of Classification Search
CPC ....... C12Q 1/37; C12Q 1/04; G01N 2800/709
USPC ........................................................... 435/23
See application file for complete search history.

(56) References Cited

U.S. PATENT DOCUMENTS

| | | | |
|---|---|---|---|
| 3,962,039 | A | 6/1976 | Bates |
| 4,495,294 | A | 1/1985 | Nakahara et al. |
| 4,695,392 | A | 9/1987 | Whitehead et al. |
| 5,308,834 | A | 5/1994 | Scott et al. |
| 6,719,973 | B1 | 4/2004 | Ding et al. |
| 6,849,426 | B2 | 2/2005 | Chen et al. |
| 7,297,551 | B2 | 11/2007 | Ding et al. |
| 7,846,678 | B2 | 12/2010 | Pepe et al. |
| 8,349,570 | B2 | 1/2013 | Pepe et al. |
| 2007/0123466 | A1 | 5/2007 | Salmon et al. |
| 2007/0160984 | A1 | 7/2007 | Huang et al. |
| 2008/0085865 | A1 | 4/2008 | Ding et al. |

FOREIGN PATENT DOCUMENTS

| | | | |
|---|---|---|---|
| EP | 0080649 | * 8/1985 | ............... C12Q 1/00 |
| WO | 03002976 | 1/2003 | |
| WO | 2009005231 A1 | 1/2009 | |
| WO | 2010021872 | 2/2010 | |
| WO | WO 2010/021872 | * 2/2010 | ............... C12Q 1/37 |
| WO | 2012118800 | 9/2012 | |

OTHER PUBLICATIONS

Endoprep (TM), BioDtech Inc. Application Notes, XP55030412, Birmingham, AL, 35209, USA retrieved from the Internet: URL: http://www.biodtechinc.com/doc/prod_endoprep.pdf [retrieved on Jun. 19, 2012], Sep. 28, 2008, pp. 1-10.

Asakawa et al., "Application of the Limulus Test for Practical Quality Control on Endotoxin Content in Commercial Human Serum Albumin (HSA) Products. In Comparison with the Rapid Pyrogen Test", Yakugaku. Zasshi, vol. 114, No. 11, 1994, pp. 888-893.

Creput et al., "New Therapeutic Targets for Antibodies and Recombinant Proteins in Organ Transplantation", Current Opinion in Molecular Therapeutics, vol. 9, No. 2, 2007, pp. 153-159.

David, "The Interaction of Lipid A and Lipopolysaccharide with Human Serum Albumin", In: Brade, H., ed. Endotoxin in Health and Disease. New York: Marcel-Dekker, Inc., 1999, pp. 413-422.

Ding et al., "High-Performance Affinity Capture-Removal of Bacterial Pyrogen from Solutions", Journal of Chromatography B, vol. 759, 2001, pp. 237-246.

Ding et al., "The Sushi Peptides: Structural Characterization and Mode of Action Against Gram-Negative Bacteria", Cellular and Molecular Life Sciences, vol. 65, 2008, pp. 1202-1219.

Doumas et al., "Serum and urine albumin: a progress report on their measurement and clinical significance", Clinica Chimica Acta, vol. 258, No. 1, 1997, pp. 3-20.

Dubel, "Recombinant Therapeutic Antibodies", Applied Microbiology and Biotechnology, vol. 74, No. 4, 2007, pp. 723-729.

Dubose et al., "Comparison of plasma extraction techniques in preparation of samples for endotoxin testing by the Limulus amoebocyte lysate test", Journal of Clinical Microbiology, vol. 11, No. 1, Jan. 1980, pp. 68-72.

European Patent Application No. 09808609.3, Office Action, mailed Jun. 27, 2012, 9 pages.

Ghetie et al., "Large scale preparation of immunotoxins constructed with the Fab' fragment of IgG1 murine monoclonal antibodies and chemically deglycosylated ricin A chain", Journal of Immunological Methods, vol. 112, No. 2, 1988, pp. 267-277.

Hulko et al., "Inherent chaperone-like activity of aspartic proteases reveals a distant evolutionary relation to double-$\Psi$ barrel domains of AAA-ATPases", Protein Science, vol. 16, 2007, pp. 644-653.

Japanese Patent Application No. 2011-523863, Office Action, mailed Feb. 28, 2014, Office Action—3 pages, English Translation—5 pages.

Jurgens et al., "Investigation into the Interaction of Recombinant Human Serum Albumin With Re- Lipopolysaccharide and Lipid A", Journal of Endotoxin Research, vol. 8, 2002, pp. 115-126.

Kaca et al., "Hemoglobin, A Newly Recognized Lipopolysaccharide (LPS)-Binding Protein That Enhances LPS Biological Activity", The Journal of Biological Chemistry, vol. 269, No. 4, 1994, pp. 25078-25084.

(Continued)

*Primary Examiner* — Sandra Saucier
(74) *Attorney, Agent, or Firm* — Kilpatrick Townsend & Stockton LLP

(57) ABSTRACT

Provided herein are methods for detecting endotoxin or Gram negative bacteria in a sample. Kits for detecting endotoxin or Gram negative bacteria in a sample are provided.

12 Claims, 1 Drawing Sheet

(56) References Cited

OTHER PUBLICATIONS

Li et al., "Molecular Mechanisms that Govern the Specificity of Sushi Peptides for Gram-Negative Bacterial Membrane Lipids", Biochemistry, vol. 45, No. 35, 2006, pp. 10554-10562.

Li et al., "The Specificity of Sushi Peptides for Endotoxin and Anionic Phospholipids: Potential Application of POPG as an Adjuvant for Anti-LPS Strategies", Biochemical Society Transactions, vol. 34, No. 2, 2006, pp. 270-272.

Nayeem et al., "Recombinant Antibodies in Cancer Therapy", Current Protein and Peptide Science, vol. 7, No. 2, 2006, pp. 165-170.

Obayashi, "Addition of Perchloric Acid to Blood Samples for Colorimetric Limulus Test Using Chromogenic Substrate: Comparison with Conventional Procedures and Clinical Applications", Journal of Laboratory and Clinical Medicine, vol. 104, No. 3, 1984, pp. 321-330.

International Patent Application No. PCT/US2012/026935, International Preliminary Report on Patentability, mailed Sep. 12, 2013, 8 pages.

International Patent Application No. PCT/US2012/026935, International Search Report & Written Opinion, mailed Sep. 24, 2012, 12 pages.

Petsch et al., "Proteinase K Digestion of Proteins Improves Detection of Bacterial Endotoxins by the Limulus Amebocyte Lysate Assay: Application for Endotoxin Removal from Cationic Proteins", Analytical Biochemistry, vol. 259, No. 1, 1998, pp. 42-47.

Rao et al., "Molecular and Biotechnological Aspects of Microbial Proteases", Microbiology and Molecular Biology Reviews, vol. 62, No. 3, 1998, pp. 597-635.

Rasmussen et al., "Manufacture of Recombinant Polyclonal Antibodies", Biotechnology Letters, vol. 29, No. 6, 2007, pp. 845-852.

Richter et al., "Mechanism of Activation of the Gastric Aspartic Proteinases: Pepsinogen, Progastricsin and Prochymosin", Biochemical Journal, vol. 335, 1998, pp. 481-490.

Rietschel et al., "Pyrogenicity and Immunogenicity of Lipid A Complexed With Bovine Serum Albumin or Human Serum Albumin", Infection and Immunity, vol. 8, No. 2, 1973, pp. 173-177.

Roth, "Hemoglobin Enhances the Production of Tissue Factor by Endothelial Cells in Response to Bacterial Endotoxin", Blood, vol. 83, No. 10, 1994, pp. 2860-2865.

Roth et al., "Optimization of Detection of Bacterial Endotoxin in Plasma with the Limulus Test", Journal of Laboratory and Clinical Medicine, vol. 116, No. 2, 1990, pp. 153-161.

Roth et al., "Production of Modified Crosslinked Cell-Free Hemoglobin for Human Use: The Role of Quantitative Determination of Endotoxin Contamination", Transfusion, vol. 33, No. 11, 1993, pp. 919-924.

Roth et al., "Toxicity of Hemoglobin Solutions: Hemoglobin is a Lipopolysaccharide (LPS) Binding Protein Which Enhances LPS Biological Activity", Artificial Cells, Blood Substitutes, and Biotechnology, vol. 22, No. 3, 1994, pp. 387-398.

Rudbach et al., "Restoration of Endotoxin Activity Following Alteration by Plasma", Nature, vol. 202, 1964, pp. 811-812.

Shahriar et al., "Identification of Lipopolysaccharide-Binding Proteins in Porcine Milk", The Canadian Journal of Veterinary Research, vol. 70, Oct. 2006, pp. 243-250.

Tan et al., "Definition of Endotoxin Binding Sites in Horseshoe Crab Factor C Recombinant Sushi Proteins and Neutralization of Endotoxin by Sushi Peptides", FASEB J., vol. 14, No. 12, 2000, pp. 1801-1813.

Tsuji et al., "Use of Magnesium to Increase Sensitivity of Limulus Amoebocyte Lysate for Detection of Endotoxin", Applied Environmental Microbiology, vol. 45, No. 4, Apr. 1983, pp. 1342-1350.

U.S. Appl. No. 12/193,169, Non-Final Office Action, mailed Jan. 26, 2010, 17 pages.

U.S. Appl. No. 12/880,993, Non-Final Office Action, mailed Aug. 30, 2011, 6 pages.

U.S. Appl. No. 12/880,993, Final Office Action, mailed Dec. 6, 2011, 7 pages.

U.S. Appl. No. 12/880,993, Non-Final Office Action, mailed May 18, 2012, 8 pages.

Westphal et al., "Extraction of Bacteria with Phenol/Water", Naturforsch B: Anorg. Chem. Org. Chem. Biochem. Biophys. Biol., vol. 7B, 1952, pp. 148-155.

Xuan et al., "Circulating Tumor Necrosis Factor-Alpha Production During the Progression of Rat Endotoxic Sepsis", Chemotherapy, vol. 47, No. 3, 2001, pp. 194-202.

Xuan et al., "In Vitro Reduction of Endotoxin Concentrations with the 5S Fragment of Immunoglobulin G", Antimicrobial Agents and Chemotherapy, vol. 41, No. 7, 1997, pp. 1512-1516.

Yentis et al., "The Effects of IgG and Immune Complexes on the Endotoxin-Induced Cytokine Response", Cytokine, vol. 6, No. 3, 1994, pp. 247-254.

Zhang et al., "Differential Blocking of Coagulation-Activating Pathways of Limulus Amebocyte Lysate", Journal of Clinical Microbiology, vol. 32, No. 6, Jun. 1994, pp. 1537-1541.

Zhu et al., "Bacterial Killing in Gastric Juice-Effect of pH and Pepsin on *Escherichia Coli* and *Helicobacter Pylori*", Journal of Medical Microbiology, vol. 55, Sep. 2006, pp. 1265-1270.

European Patent Application No. 12752574.9, Extended European Search Report, mailed Sep. 26, 2014, 6 pages.

\* cited by examiner

*Plasma Protein Digestion with EndoPrep™ Treatment.*
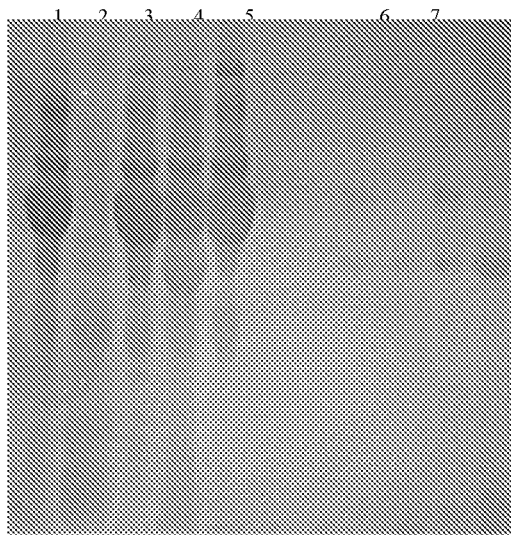
1. 1:10 Dilution, pH 4.5
2. 1:10 Dilution, pH 1.0
3. 1:10 Dilution, pH 6.0
4. 1:10 Dilution, pH 4.5 (high conc.)
5. 1:10 Dilution, No Treatment
6. 1:100 Dilution, pH 4.5
7. 1:100 Dilution, pH 1.0
8. 1:100 Dilution, pH 6.0
9. 1:100 Dilution, pH 4.5 (high conc.)
10. 1:100 Dilution, No Treatment

ENHANCING ENDOTOXIN DETECTION

BACKGROUND

Endotoxin, also known as lipopolysaccharide (LPS), is an integral component of the Gram-negative bacterial cell membrane and is responsible for many, if not all, of the toxic effects that occur during Gram-negative bacterial sepsis. LPS is a mixture of glycolipids consisting of a variable polysaccharide domain covalently bound to a conserved glucosamine-based phospholipid known as lipid A. LPS directly stimulates host monocytes and macrophages to secrete a wide array of inflammatory cytokines that include tumor necrosis factor-I (TNF-I), interleukin-1 (IL-1), and interleukin-8 (IL-8). Excessive release of these cytokines by host macrophages contributes to organ failure and death that occur after episodes of Gram-negative bacterial sepsis.

SUMMARY

Provided herein are methods for detecting endotoxin in a sample, including, for example, a citrated or EDTA-containing sample. For example, provided herein is method of detecting endotoxin in a sample comprising heating the sample; acidifying the heated sample to a pH of about 1 to 4; contacting the acidified sample with an acidic protease; increasing the pH of the protease-treated sample to about 6 to 8; and detecting endotoxin in the sample.

Also provided herein are kits for detecting endotoxin in a sample, including, for example, a citrated or EDTA-containing sample. The details of one or more aspects are set forth in the accompanying description below. Other features, objects and advantages will be apparent from the description and from the claims.

BRIEF DESCRIPTION OF THE FIGURES

FIG. 1 shows plasma protein digestion with EndoPrep™ treatment.

DETAILED DESCRIPTION

Since endotoxin contains a negative charge, a lipid and a carbohydrate, certain molecules can interfere with the ability of assays to properly measure endotoxin. Provided herein are improved methods and kits for detecting endotoxin in a sample. For example, provided herein is method of detecting endotoxin in a sample comprising heating the sample; acidifying the heated sample to a pH of about 1 to 4; contacting the acidified sample with an acidic protease; increasing the pH of the protease-treated sample to about 6 to 8; and detecting endotoxin in the sample. Optionally, the method can further comprise inactivating the acidic protease after contacting the sample with an active protease and before detecting endotoxin in the sample. Optionally, the acidic protease is inactivated by a pH of about 7.0.

In the methods set forth herein, the sample can be, for example, a biological sample or an environmental sample. As used herein, a biological sample subjected to testing is a sample derived from a subject such as a mammal or human and includes, but is not limited to, any biological fluid, including a bodily fluid. Examples of bodily fluids include, but are not limited to, whole blood, plasma, serum, urine, saliva, ocular fluid, ascites, spinal fluid, tissue infiltrate, pleural effusions, lung lavage fluid, and the like. The biological fluid includes a cell culture medium or supernatant of cultured cells. For example, the sample can be a blood sample or a serum sample. Optionally, the sample is a liquid sample, such as water or other agents used, for example, in research or clinical laboratories or hospitals. The sample can also be from a commercial source.

As used herein, an environmental sample includes, but is not limited to, fluid, waste, water, dust and rain samples. Optionally, the environmental sample is obtained from a surface, for example, in a hospital, for analysis in the provided methods. For example, a sample can be obtained from a device used in a hospital, clinical or laboratory setting and analyzed for the presence of Gram negative bacteria. Optionally, the sample is diluted in solution prior to analysis.

A device used in a hospital, clinical or laboratory setting can be, but is not limited to a medical device such as a tube, a stent, a hemodialysis membrane, a filter, a mesh, a bandage or any other product that comes in physical contact with a patient during diagnosis, prevention, therapy or surgery. A medical device can also be an instrument or a component of an instrument utilized during diagnosis, prevention, therapy or surgery. A device can also be a laboratory instrument, such as a centrifuge, a microscope, a laboratory hood, etc.

The presence of anticoagulants such as, for example, sodium citrate or EDTA can cause variation in standard assays, resulting in false positives and negatives, as well as affecting accuracy. Therefore, the sample to be tested can comprise a citrated or EDTA-containing sample which interferes with endotoxin assays. For example, the sample can comprise citrated plasma or EDTA treated plasma.

In the methods described herein, the sample can be heated to a temperature of about 60° C. to about 70° C. Therefore, the sample can be heated to a temperature of about 60° C., 61° C., 62° C., 63° C., 64° C., 65° C., 66° C., 67° C., 68° C., 69° C. or about 70° C. The sample can be heated for about 20 to about 40 minutes. For example, the sample can be heated for about 40, 39, 38, 37, 36, 35, 34, 33, 32, 31, 30, 29, 28, 27, 26, 25, 24, 23, 22, 21 or about 20 minutes. The sample can be cooled after heating to about, for example, 18° C. to about 25° C. Therefore, the sample can be cooled to about 18° C., 19° C., 20° C., 21° C., 22° C., 23° C., 24° C. or to about 25° C.

In the methods set forth herein, the sample can be acidified by adding an acid to the sample. For example, hydrochloric acid can be added to the sample to obtain a pH of about 1 to about 4. The acid can be at a molarity that one of the skill in the art can use to acidify a sample to a pH of about 1 to about 4. For example, the acid can be 1M HCl. Other acids include, but are not limited to, nitric acid, sulfuric acid and acetic acid. Optionally, an alkaline phosphatase inhibitor can be included when acidifying the sample.

In the methods set forth herein, the sample can be contacted with an active acidic protease at a pH of less than 4, less than 3, less than 2 or about 1. Therefore, the pH can be about 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1 or about 1.0. Prior to acidifying the sample, the sample can be diluted to about 1 part sample to about 10 parts diluent. For example, the sample can be diluted to about 1 part sample to about 1 part diluent, to about 1 part sample to about 2 parts diluent, to about 1 part sample to about 3 parts diluent, to about 1 part sample to about 4 parts diluent, to about 1 part sample to about 5 parts diluent, to about 1 part sample to about 6 parts diluent, to about 1 part sample to about 7 parts diluent, to about 1 part sample to about 8 parts diluent, to about 1 part sample to about 9 parts diluent or to about 1 part sample to about 10 parts diluent. The diluent can be, but is not limited to, a buffer comprising divalent cations, for example a Tris buffer comprising $MgCl_2$ or a Tris buffer comprising $CaCl_2$.

As used herein, acid, acidic, aspartic or aspartic acid proteases refer to proteases active at low pH. For example, the protease is active at a pH from about 0.0 to about 6.0 or any pH between 0.0 and 6.0, inclusive. Such proteases are inactive at a pH of about 6.0 to about 14.0. As used herein, an inactive acidic protease refers to a protease without proteolytic activity (i.e., a protease that is unable to cleave an amino acid sequence such as a polypeptide or protein). As used herein, an active acidic protease refers to a protease with proteolytic activity (i.e., a protease that is able to cleave an amino acid sequence). By way of example, an active acidic protease can be inactivated by a pH of 6.5 or higher (i.e., the protease is in a solution with a pH of 6.5 or higher). The pH of a solution can be altered by addition of chemicals to a solution. For example, hydrochloric acid can be used to reduce pH and sodium hydroxide can be used to raise pH. Phosphoric acid can be used to maintain a pH of about 6.5. Optionally, a pepsin inhibitor is used to inactivate pepsin. Pepsin inhibitors include, but are not limited to, acetamidine, N-acetyl-D-phenyalanyl-L-diiodotyrosine, N-acetyl-L-phenyalanyl-D-phenylalanine, p-aminobenzamidine, benzamidine, butyamine, diazoketones, ethylamine, pepstatin, and phenylactamidine.

Acid or acidic proteases, such as endopeptidases, are known and have been grouped into three families, namely, pepsin (A1), retropepsin (A2), and enzymes from pararetroviruses (A3). The members of families A1 and A2 are known to be related to each other, while those of family A3 show some relatedness to A1 and A2. Microbial acid proteases exhibit specificity against aromatic or bulky amino acid residues on both sides of the peptide bond, which is similar to pepsin, but their action is less stringent than that of pepsin. Acid proteases include microbial, fungal, viral, animal and plant acidic proteases. Microbial aspartic proteases can be broadly divided into two groups, (i) pepsin-like enzymes produced by *Aspergillus, Penicillium, Rhizopus*, and *Neurospora* and (ii) rennin-like enzymes produced by *Endothia* and *Mucor* spp (Rao et al., *Microbiology and Molecular Biology* 62(3):597-635 (1998); Richter et al., *Biochem. J.* 335:481-90 (1998)). Examples of acidic proteases include, but are not limited to, pepsins, including pepsins A, B and C; rennin; chymosin; plasmepsin; cathepsins, such as, for example, cathepsin D and cathepsin E; human urinary acid protease; and viral proteases like HIV protease. Fungal proteases include, but are not limited to, fungal proteases derived from *Neurospora oryzae, Mucor pusillus, Mucor miehei, Aspergillus niger, Rhizopus chinensis*, or *Endothia parasitica*. Microbial proteases include, but are not limited to, yeast proteinase A, aspergillopepsinogen, rhizopuspepsin, penicillopepsin, and endothiapepsin.

In the methods set forth herein, the pH of a protease-treated sample can be increased to a pH greater than 6, greater than 6.5, greater than 7, greater than 7.5 or about 8 by addition of a base to the protease-treated sample. Therefore, the pH can be about 6, 6.1, 6.2, 6.3, 6.4, 6.5, 6.6, 6.7, 6.8, 6.9, 7.0, 7.1, 7.2, 7.3, 7.4, 7.5, 7.5, 7.7, 7.8, 7.9 or about 8. The base can be at a normality that one of skill in the art can use to increase the pH of a sample from about 6 to about 8. For example, 0.5 N sodium hydroxide can be used to increase pH. Other examples of bases include, but are not limited to, potassium hydroxide and ammonia. Prior to increasing the pH of the sample, from about 6 to about 8, the sample can be diluted to about 1 part sample to about 10 parts diluent. For example, the sample can be diluted to about 1 part sample to about 1 part diluent, to about 1 part sample to about 2 parts diluent, to about 1 part sample to about 3 parts diluent, to about 1 part sample to about 4 parts diluent, to about 1 part sample to about 5 parts diluent, to about 1 part sample to about 6 parts diluent, to about 1 part sample to about 7 parts diluent, to about 1 part sample to about 8 parts diluent, to about 1 part sample to about 9 parts diluent or to about 1 part sample to about 10 parts diluent. The diluent can be, but is not limited to a buffer comprising divalent cations, for example a Tris buffer comprising $MgCl_2$ or a Tris buffer comprising $CaCl_2$.

Endotoxin can be detected via methods standard in the art, for example, and not to be limiting, these include gel-clot assays, turbidimetric assays, and chromogenic assays. The PyroGene® Recombinant Factor C Endotoxin detection System (Lonza 50-658U) is an example of a fluorescence assay that can be utilized. It is understood that since endotoxin is an integral component of the Gram-negative bacterial cell membrane, the methods set forth herein can also be utilized to detect the presence of Gram negative bacteria in a sample.

Kits for detecting endotoxin, Gram negative bacteria or lipopolysaccharide are provided. The kits comprise an acidic protease, an acid and a base. The acid can be, for example, hydrochloric acid, nitric acid, sulfuric acid or acetic acid, to name a few. The acid can be at a molarity that one of skill in the art can use to acidify a sample to a pH of about 1 to about 4. For example, the acid can be about 1M HCl. The base can be, for example, sodium hydroxide, ammonia, or potassium hydroxide, to name a few. The base can be at a normality that one of skill in the art can use to increase the pH of a sample from about 6 to about 8. For example, the base can be about 0.5N NaOH. As discussed above, the acidic protease can be any acidic protease. For example, the acidic protease is selected from the group consisting of pepsin, rennin, chymosin, plasmepsin, cathepsin D, cathepsin E, human urinary acid protease, HIV protease, *Neurospora oryzae* protease, *Mucor pusillus* protease, *Mucor miehei* protease, *Aspergillus niger* protease, *Rhizopus chinensis* protease, *Endothia parasitica* protease, yeast proteinase A, aspergillopepsinogen, rhizopuspepsin, penicillopepsin, and endothiapepsin. Optionally, the kits further comprise one or more buffers, such as, for example, an acidic protease buffer. Optionally, the kits further comprise an alkaline phosphatase inhibitor.

Disclosed are materials, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that, while specific reference to each various individual and collective combinations and permutation of these compounds may not be explicitly disclosed, each is specifically contemplated and described herein. For example, if a method is disclosed and discussed and a number of modifications can be made to materials used in the method or in the steps of the method, each and every combination and permutation of the method and the modifications that are possible are specifically contemplated unless specifically indicated to the contrary. Likewise, any subset or combination of these is also specifically contemplated and disclosed. Thus, if there is a variety of additional steps that can be performed in a method, it is understood that each of these additional steps can be performed with any specific method steps or combination of method steps of the disclosed methods, and that each such combination or subset of combinations is specifically contemplated and should be considered disclosed. Thus, a number of aspects have been described. Nevertheless, it will be understood that various modifications may be made. Furthermore, when one characteristic or step is described, it can be combined with any other characteristic or step herein even if the combination is not explicitly stated. Accordingly, all combination of disclosed agents, steps and characteristics are provided even in the absence of explicit disclosure herein.

Ranges may be expressed herein as from about one particular value, and/or to about another particular value. When such a range is expressed, this includes from the one particular value and/or to the other particular value. Similarly, when values are expressed as approximations, by use of the antecedent about, it will be understood that the particular value is disclosed.

Throughout this application, various publications are referenced. The disclosures of these publications in their entireties are hereby incorporated by reference into this application.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and materials provided herein.

EXAMPLES

In the following examples, an endotoxin spike refers to the defined amount of exogenous endotoxin added to the plasma samples prior to treatment. The ability to detect the spike after treatment dictates the success of the protocol. Each set of experiments included a set of treated controls. These controls were identical to the samples but contained water instead of plasma. These samples were diluted in the same buffers and incubated under identical conditions. Each set of experiments included a set of untreated controls. These controls were prepared using identical handling and dilution procedures but using endotoxin-free water immediately prior to testing. Recovery is defined as the percentage of endotoxin spike detected in the treated samples as compared to the control samples. Every replicate of every sample was performed both with and without a 1 EU/ml Positive Product Control (PPC) according to industry standards. The PPC is a sample of product to which a known amount of endotoxin spike has been added. It is used as a monitor of product inhibition or enhancement. Industry standards dictate that a PPC value of 50-200% represents an acceptable assay.

Set forth below are experiments for accurate endotoxin detection in blood-derived products. The first set of experiments showed that heat-inactivation alone was insufficient for detection (Table 1). The second set of experiments involved digestion of the samples with the EndoPrep™ system. These results also indicated a lack of detection accuracy (Table 2). The third set of experiments involved a combination of heat-inactivation and EndoPrep™ digestion. These results showed adequate PPC data but poor spike recovery (Table 3). Alteration of pH resulted in more efficient digestion (FIG. 1) without causing product insolubilization. By changing the "spike-point" (Table 4-5) it was determined that there was a pH- and heat-sensitive component in plasma that prevented spike recovery. After addressing these issues, and testing the protocol with crude environmental endotoxin, the protocol was tested with citrated plasma and showed acceptable results at a 1:100 final dilution (Table 6).

Heat Inactivation

A heat inactivation protocol was performed on all samples. These results are from 30 minute incubations in the Lonza® PyroGene assay using a polynomial standard curve based on endotoxin standards provided with the kit. Each set of data represents triplicate testing using 10 unique plasma/serum samples (5 male, 5 female).

TABLE 1

Heat Inactivation of Normal Samples.

| Sample | Dilution | % Spike Recovery | % PPC Recovery |
|---|---|---|---|
| Citrated Plasma | 1:10 | 21.0% | 1.9% |
| | 1:100 | 4.9% | 182.7% |
| | 1:1000 | 12.3% | 162.5% |
| Heparinized Plasma | 1:10 | 139.0% | −2.9% |
| | 1:100 | 90.7% | 2.7% |
| | 1:1000 | 375.8% | −3.8% |
| Serum | 1:10 | 21.2% | 2.3% |
| | 1:100 | 15.0% | 5.7% |
| | 1:1000 | 14.9% | 0.3% |

The low to negative PPC values associated with heparinized plasma and serum suggest that the spike recovery numbers are endotoxin-independent and are a result of interfering factors in the sample that persist after heat treatment. The citrated plasma data give marginally acceptable PPC results and low recovery at the 1:100 and 1:1000 dilutions. These results demonstrate that heat-inactivation alone is insufficient for endotoxin detection.

Endoprep™ Treatment

An EndoPrep™ treatment protocol was performed on all samples. Briefly, plasma samples were diluted 1:10 in BDTI Digestion Buffer (i.e. 270 ul buffer+30 ul plasma). To this mixture 30 μl of BDTI Protease Solution was added and mixed with vortexing. The solution was incubated in a 37° C. water bath for 60 minutes. The solutions were then diluted 1:10 and 1:100 in endotoxin-free water and tested for endotoxin in the PyroGene assay.

After treatment, the samples were subjected to Lonza® PyroGene testing. These results are from 30-minute incubations in the Lonza® PyroGene assay using a polynomial standard curve based on endotoxin standards provided with the kit. Each set of data represents triplicate testing using 10 unique plasma/serum samples (5 male, 5 female).

TABLE 2

EndoPrep ™ Treatment of Normal Samples.

| Sample | Dilution | % Spike Recovery | % PPC Recovery |
|---|---|---|---|
| Citrated Plasma | 1:100 | 353.8% | 38.4% |
| | 1:1000 | 265.8% | 198.3% |
| Heparinized Plasma | 1:100 | 212.3% | 5.0% |
| | 1:1000 | 27.5% | 381.4% |
| Serum | 1:100 | 2470.0% | 0% |
| | 1:1000 | 2157.7% | 297.0% |

The PPC data show a pattern of low recovery at 1:100 and excessive recovery at 1:1000. This pattern is a result of saturation caused by the excessively high spike recovery data at 1:100. Summarily, this shows that both the PPC and recovery data are significantly higher than the controls. There were samples of citrated plasma at the 1:1000 dilution that gave acceptable results. These results demonstrate that EndoPrep™ treatment alone is insufficient for endotoxin detection in citrated plasma.

Heat Inactivation+Endoprep Treatment

A heat inactivation+EndoPrep™ treatment protocol was performed on all samples with the addition of a 60-minute room temperature equilibration step. These results are from 30-minute incubations in the Lonza® PyroGene assay using a polynomial standard curve based on endotoxin standards provided with the kit. Each set of data represents triplicate testing using 10 unique plasma/serum samples (5 male, 5 female).

TABLE 3

Heat Inactivation + EndoPrep ™ Treatment of Normal Samples.

| Sample | Dilution | % Spike Recovery | % PPC Recovery |
|---|---|---|---|
| Citrated Plasma | 1:100 | 3.2% | 80.4% |
|  | 1:1000 | 5.5% | 78.7% |
| Heparinized Plasma | 1:100 | 34.6% | 27.4% |
|  | 1:1000 | 20.9% | 124.3% |
| Serum | 1:100 | 7.3% | 65.4% |
|  | 1:1000 | 10.1% | 83.5% |

There was a similar pattern with all three sample types: poor spike recovery but acceptable PPC recovery. The most appealing result was PPC recovery over 80% in citrated plasma at the 1:100 dilution. This indicates that the sample that is going into the assay is amenable for the endotoxin detection but the spike is not detected. This suggests that the spike is being either inactivated or masked during treatment. Extensive control reactions show that no part of the treatment (i.e., heat-inactivation, EndoPrep™ digestion, incubation, dilution in Tris, etc.) adversely affects endotoxin. These results demonstrate that a combination of heat-inactivation and EndoPrep™ treatment is sufficient for endotoxin detection but the endotoxin "spike" is being destroyed or masked by an unknown plasma/serum component.

Reduction Of Endogenous Endotoxin-Inactivating Activity

The initial hypothesis was that plasma/serum proteins were binding endotoxin and then becoming insoluble during treatment. This would cause the endotoxin to be in an insoluble form and therefore undetectable. Further treatment indicated that plasma/serum samples could exhibit insolubility if allowed to incubate at 37-65° C. at a pH range from approximately 4.5 to 6. The protocol was amended to avoid this pH range by decreasing the EndoPrep™ digestion pH to 1-2. As set forth above, this pH can be decreased from about 1 to about 4. This resulted in more efficient protein digestion as indicated by PAGE results although it did not restore adequate spike recovery (See FIG. 1)

The next hypothesis was that a plasma/serum component was inactivating endotoxin. Surprisingly, the sourced samples were at a pH of 8.3, indicating that alkaline enzymes (such as alkaline phosphatase) would be active. To test this, samples of citrated plasma were tested at a 1:100 dilution with the current protocol with different "spike-points." One sample was treated as normal. A second sample (post-pH) was pH adjusted to an acidic range prior to adding the endotoxin spike. A third sample (post-Heat) was pH adjusted to an acidic range and heat-inactivated prior to adding the endotoxin spike.

TABLE 4

Heat Inactivation + EndoPrep ™ Treatment of Samples with Various "Spike-Points".

| Sample | % Spike Recovery | % PPC Recovery |
|---|---|---|
| Normal | 2.4-3.3% | 158.0% |
| Post-pH | 20.7-28.8% | 67.6% |
| Post-Heat | 29.4-40.8% | 143.7% |

The post-Heat experiment was then repeated with a few alterations (e.g., increased heat-inactivation time, increased EndoPrep™ digestion time, alteration of divalent cation addition, etc.) to maximize recovery:

TABLE 5

Optimization of Post-Heat "Spike-Point" Sample.

| Sample | % Spike Recovery | % PPC Recovery |
|---|---|---|
| Post-Heat | 50.1-105.5% | 76.9-81.0% |

These results demonstrate that there is a plasma component that is interfering with endotoxin detection. It is both pH- and heat-sensitive. It is necessary to incorporate a treatment step at the time of sample collection to inactivate this component to make endotoxin detection possible.

Developing A Protocol

The last alteration of the protocol was to test it using crude, environmental endotoxin rather than purified endotoxin. A sample of bacteria was grown, lysed, and diluted in endotoxin-free water. This endotoxin stock resulted in even more efficient recovery and was used as the "spike" to test the protocol.

The protocol incorporates the following:

Heat-inactivation step at the time of collection to inactivate endogenous factors that interfere with endotoxin detection.

Involves pH manipulation that results in optimal EndoPrep™ and Lonza® PyroGene activity and avoids insolubilization.

Detects crude, environmental endotoxin.

A final dilution of only 1:100 allowing minimum detection in the 0.1-1.0 EU/ml range.

The following is an example of a protocol that can be used to detect endotoxin in citrated plasma. The results are set forth in Table 6.

1. Add 100 µl citrated plasma to a 12×75 mm borosilicate glass culture tube.
2. Heat sample in a 65±1° C. water bath for 30 minutes.
3. Cool to 18-25° C.
4. Remove 30 µl sample and transfer to a new endotoxin-free culture tube.
5. Add 3 µl endotoxin stock solution and vortex for 5-10 seconds.
6. Add 270 µl 10 mM Tris pH 1.0 containing 0.75 µM $MgCl_2$.
    a. Lower final pH to 1-2 using 1 M HCl.
    b. Typical samples require approximately 8 µl M HCl.
    c. Test final pH with pH-Indicator Strips.
7. Add 30 µl BDTI Protease Solution and vortex for 5-10 seconds.
8. Incubate sample in a 37±1° C. shaking water bath for 180 minutes at an oscillation speed of 150 strokes/minutes.
9. In an endotoxin-free tube mix 50 µl sample with 450 µl 10 mM Tris pH 7.0.
    a. Raise final pH to 6-8 using 0.5 N NaOH.
    b. Typical samples require approximately 5 µl 0.5 N NaOH.
    c. Test final pH with pH-Indicator Strips.
10. Allow sample to equilibrate for 60 minutes.
11. Test samples with and without 1 EU/ml PPC using the Lonza® PyroGene assay according to manufacturer's specifications.

TABLE 6

Protocol for Treatment of Citrated Plasma.

| Sample | % Treated Spike Recovery (±SD) | % PPC Recovery (±SD) | % Recovery (±SD) (Normalized to % PPC) |
|---|---|---|---|
| All (#1-10) | 77.2 ± 26.7% | 89.3 ± 12.8% | 87.0 ± 28.6% |
| Males (#1-5) | 91.7 ± 18.1% | 90.5 ± 14.3% | 101.8 ± 16.3% |
| Females (#6-10) | 72.9 ± 17.8% | 86.5 ± 12.1% | 84.6 ± 19.7% |

What is claimed is:

1. A method of detecting endotoxin in a sample comprising:
   a) heating the sample to a temperature of about 60° C. to about 70° C.;
   b) acidifying the heated sample to a pH of about 1 to 4;
   c) contacting the acidified sample with an acidic protease;
   d) increasing the pH of the protease-treated sample to about 6 to 8 and
   e) detecting endotoxin in the sample.

2. The method of claim 1, wherein the sample is a biological sample or an environmental sample.

3. The method of claim 2, wherein the biological sample is selected from the group consisting of plasma, blood, serum, ascites, pleural fluid, ocular fluid and spinal fluid.

4. The method of claim 3, wherein the plasma is citrated plasma or EDTA collected plasma.

5. The method of claim 2, wherein the environmental sample is selected from the group consisting of fluid, waste, water, dust and rain.

6. The method of claim 2, wherein the biological sample is diluted to about 1 part sample to about 10 parts diluent prior to step b).

7. The method of claim 6, wherein the diluent is a Tris solution comprising $MgCl_2$.

8. The method of claim 2, wherein the biological sample is diluted to about 1 part sample to about 10 parts diluent prior to step d).

9. The method of claim 8, wherein the diluent is a Tris solution.

10. The method of claim 9, wherein the Tris solution is at a pH of about 6 to 8.

11. The method of claim 1, wherein the acidic protease is pepsin.

12. The method of claim 1, further comprising inactivating the acidic protease.

* * * * *